(12) United States Patent
Goodman et al.

(10) Patent No.: US 7,087,228 B2
(45) Date of Patent: Aug. 8, 2006

(54) PREVENTING TOOTH DECAY AND INFECTIVE ENDOCARDITIS USING NATURAL OLIGOPEPTIDES

(75) Inventors: Steven D. Goodman, Redondo Beach, CA (US); Olga Kay, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 76 days.

(21) Appl. No.: 10/614,072

(22) Filed: Jul. 2, 2003

(65) Prior Publication Data

US 2004/0105824 A1    Jun. 3, 2004

Related U.S. Application Data

(60) Provisional application No. 60/393,712, filed on Jul. 3, 2002.

(51) Int. Cl.
*A61K 39/40* (2006.01)
*C07H 21/04* (2006.01)
*C07K 16/00* (2006.01)

(52) U.S. Cl. ............... 424/165.1; 536/23.7; 530/388.4
(58) Field of Classification Search ............... 530/340, 530/388.4; 424/97.1, 164.1, 165.1; 536/23.7
See application file for complete search history.

(56) References Cited

U.S. PATENT DOCUMENTS

| | | |
|---|---|---|
| 4,692,407 A | 9/1987 | Jordan et al. |
| 4,725,576 A | 2/1988 | Pollock et al. |
| 5,013,542 A | 5/1991 | Hay et al. |
| 5,374,538 A | 12/1994 | Bratthall |
| 5,486,503 A | 1/1996 | Oppenheim et al. |
| 5,631,228 A | 5/1997 | Oppenheim et al. |
| 5,646,119 A | 7/1997 | Oppenheim et al. |
| 5,801,226 A | 9/1998 | Cummins et al. |
| 5,807,541 A | 9/1998 | Aberg et al. |
| 5,830,489 A | 11/1998 | Valenti et al. |
| 5,885,965 A | 3/1999 | Oppenheim et al. |
| 5,912,230 A | 6/1999 | Oppenheim et al. |
| 6,136,298 A | 10/2000 | Gaffar et al. |
| 6,231,857 B1 | 5/2001 | Shi et al. |
| 2002/0081302 A1* | 6/2002 | Cvitkovitch et al. ...... 424/164.1 |

OTHER PUBLICATIONS

Ooshima, T. et al, Cariostatic activity of cacao mass extract, Archives of oral biology, Sep. 2000, 45(9) p. 805-8.*
Kuramitsu, H. et al, Immunological relationships between glucosyltransferase from streptococcus mutans serotypes, Infection and Immunity, Sep. 1976, 14(3), p. 636-44.*
Thomas E. Creighton, in his book, "Proteins: Structures and Molecular Properties, 1984", (pp. 314-315).*
Thomas E. Creighton, in his book Protein Structure: A Practical Approach, 1989; pp. 184-186.*
Nosoh, Y. et al in "Protein Stability and Stabilization through Protein Engineering, 1991" (chapter 7, p. 197, second paragraph).*
Kumar, V. et al (Amino acid variations at a single residue in an autoimmune peptide profoundly affect its properties: T-cells activation . . . , Immunology, 1990; 87: 1337-1341).*
Zero, Sugars- The arch Criminal!, Caries Research, 2004; 38: 277-285.*
Idone et al (Effect of an orphan response regulator on Streptococcus mutans sucrose-dependent adherence and cariogenesis, Infection and Immunity, 2003; 71(8): 4351-4360).*
Clark et al (Influence of salivary components and extracellular polysaccharide synthesis from sucrose on the attachment of streptococcus mutans 6715 to hydroxyapatite surfaces, Infection and Immunity, 1977; 18(2): 514-523).*
Keys (Infective Endocarditis, The Cleveland Clinic, 2004; 1-12).*
Ellen, R.P., Microbiological Assays for Dental Caries and Peridontal Disease Susceptibility, *Oral Sci. Rev.* 8:3-23 (1976).
Fukushima, K., Okada, T., Ochiai, K. "Production Characterization and Application of Monoclonal Antibodies which Distinguish Three Glucosyltransferases from *Streptococcus Mutans*," *Infection and Immunity* 61:323-328 (1993).
Goodman, S.D. and Gao Q., "Firefly Luciferase as a Reporter to Study Gene Expression in *Streptococcus Mutans*," *Plasmid* 42:154-157 (1999).
Goodman, S.D. and Gao, Q. "Characterization of the *gtfB* and *gtfC* promoters from *Streptococcus Mutans* GS-5," *Plasmid* 43:85-98 (2000).
Goodman, et al. "In Vitro Selection of Integration Host Factor Binding Sites," *J. of Bact.* 181-2346-3255 (1999).
Hanada, N., Kuramitsu, H.K., "Isolation and Characterization of the *Streptococcus Mutans gtfD* Gene Coding for Primer-Dependent Soluble Glucan Synthesis," *Infection and Immunity*, 57:2079-2085 (1989).

(Continued)

*Primary Examiner*—Lynette R. F. Smith
*Assistant Examiner*—Lakia J. Tongue
(74) *Attorney, Agent, or Firm*—Hogan & Hartson LLP

(57) ABSTRACT

The present invention provides compositions, medicaments, and methods for the treatment or prophylaxis of conditions associated with the binding of *Streptococcus mutans* to teeth. Specifically, the present invention provides a method for preventing dental caries and infective endocarditis in a subject by treating the subject's oral cavity with a composition or medicament comprising the competence stimulating peptide (CSP) of the causative bacterium, which inhibits the ability of the said bacteria to attach to the surface of teeth. Novel anti-caries compositions using the CSP are also disclosed.

16 Claims, 11 Drawing Sheets

OTHER PUBLICATIONS

Hume, W.R., "Need for Change in Standards of Caries Diagnosis-Perspective Based on the Structure and Behavior of the Carious Lesion," *J. Dent. Educ.* 57:439-443 (1993).

Igarashi et al., "Direct Detection of *Streptococcus Mutans* in Human Dental Plaque by Polymerase Chain Reaction," *Oral Microbiol an Immunol.* 11:294-298 (1996).

Lee, M.S. and Morrison, D.A., "Identification of a New Regulator in *Streptococcus Pneumociae* Linking Quorum Sensing to Competence for Genetic Transformation," *J. of Bact.* 181:5004-5016 (1999).

Lenander-Lumikari et al., "Saliva and Dental Caries," *Adv. Dent. Res.* 14:40-47 (Dec. 2000).

Li, Y-H et al., "Natural Genetic Transformation of *Streptococcus Mutans* Growing in Biofilms," *J. of Bac.* 183:897-908 (2001).

Tanzer, J.M., "Understanding Dental Caries; an Infectious Disease, not a Lesion," *Inter. J. Oral Biol.* 22:205-214 (1997).

* cited by examiner

FIGURE 1

SGSLSTFFRLFNRSFTQALGK  (SEQ ID NO: 1)

CSP added:    none    5 mcg/ml

Panel 1: anti-*gtf* (glucosyltransferase) antibody

Panel 2: anti-*ftf* (fructosyltransferase) antibody

FIGURE 10

```
          -11
           |
  gtfB    ACAATTATAACGTTTTGAATAAA*ACAGTTTAA
           ||| ||     |   ||||  ||||||  ||||||  |
ComE Box  aCAtTTcRGWWWWWWWWWWWWWW*ACAGTTgAG
           ||| | |     |  |||||||||  ||  |||   |
  gtfC    ACAATACTAGTGTTTTATATCAAAACACTAACT
```

PREVENTING TOOTH DECAY AND INFECTIVE ENDOCARDITIS USING NATURAL OLIGOPEPTIDES

CROSS-REFERENCE TO RELATED APPLICATIONS

This application claims the benefit under 35 U.S.C. § 119(e) of U.S. Provisional Application No. 60/393,712 filed Jul. 3, 2002, which is incorporated herein by reference in its entirety.

BACKGROUND OF THE INVENTION

1. Field of the Invention

The present invention provides compositions, medicaments and methods for the prevention or prophylaxis of dental caries and infective endocarditis.

2. Description of the State of the Art

Dental caries is an undesirable condition of the oral cavity and, over the years, has remained an intractable disease. Caries is a unique multifactorial infectious disease. (Lenander-Lumikari et al., Adv. Dent. Res. 14: 40–47 (December 2000)). Dental caries affects teeth at all levels and can cause extensive crown mutilations, bacterial disorders of the periapical tissues, or even loss of the affected dental elements. Clinically, the disease is characterized by demineralization of the dental enamel and of the dentin in various stages of progress until it affects the pulp space. When the lesion passes beyond the enamel-dentin border, a phlogistic reaction of the pulp tissues is constantly observed, with the formation of reaction dentin in some cases. Approximately 50% of adults have at least four caries-related lesions that have been treated or require treatment, and approximately 30% of adults have over 50% of their teeth affected by caries. With advances in science and technology, newer methods have been introduced to combat this disease but the search for an acceptable treatment continues.

Efforts toward the correction of dental caries have revolved around the use of the standard toothbrush to remove dental plaque. Also in widespread use today are electric brushes, floss and adjuncts such as proxy brushes. In addition, numerous toothpastes and mouth rinses containing various supplements that are touted as aids in the prevention of dental caries. For example, fluoride is commonly sold as a product for slowing the process of dental decay. However, the efficacy of such methods of treating or preventing dental caries is questionable. Dental plaque can only partially be removed from the oral cavity, even when a demanding regimen of oral hygiene that may include flossing, brushing and regular visits to a dentist is followed. In addition, many toothpastes and mouth rinses contain toxic supplements such as fluoride and triclosan that can be toxic to very young children. Further, most oral bacteria are benign and are actually important for oral health. Consequently, an overall reduction in oral bacteria is not a practical means to prevent tooth decay. For example, when the level of certain oral bacteria is reduced (e.g., after prolonged use of antibiotics), an overgrowth of indigenous yeast occurs, resulting in a disorder known as Thrush.

In the last half century, it has become clear that dental plaque actually consists of hundreds of different bacterial taxa. Most of these bacteria exist on the surface of teeth in heterogeneous communities called plaque or biofilms. The mouth thus acts as a reservoir for these bacteria. While most of these bacteria are commensal, meaning they fail to adversely affect the human host, others are pathogenic and can cause tooth decay. Moreover these pathogenic bacteria have been found to cause a life-threatening disease called endocarditis.

Among all of these bacteria, the primary etiologic agent of tooth decay is the bacterium *Streptococcus mutans*. *S. mutans* is a resident of the biofilm environment of dental plaque, a matrix of bacteria and extracellular material that adheres to the tooth surface. Under appropriate environmental conditions populations of *S. mutans* and the pH of the surrounding plaque will drop. *S. mutans*, being among the most acid tolerant organisms residing in dental plaque, will increase it numbers in this acidic environment and eventually become a dominant member of the plaque community. Once attached, *S. mutans* inflicts its damage by fermenting simple dietary sugars into lactic acid. This situation eventually leads to dissolution of the tooth enamel, resulting in the development of dental caries. Since there is a strong correlation between the proportion of *S. mutans* in dental plaque or in saliva relative to other bacterial species and the presence or risk of future outbreaks of dental caries, *S. mutans* in plaque or saliva may serve as an index for both caries activity state and caries risk or susceptibility. These indices play an increasingly important role in the diagnosis and treatment of dental caries. (Hume, W. R., *J. Dent. Educ.* 57: 439–443 (1993)).

*S. mutans* has also been found to contribute to infective endocarditis. Infective endocarditis is a potentially lethal infection of both native (normal) and artificial heart valves, and if left untreated can be fatal. *S. mutans* form biofilms on the surface of these valves, and are typically a mixed community of a variety of pathogenic bacteria. Since the these bacteria find their way to the valves via the blood stream and the blood stream is typically aseptic, there are usually few opportunities for bacteria to cause these infections. One exception is when pathogenic bacteria like *S. mutans* enter the blood stream during dental procedures. Hence, the probability of infection is directly related to the reservoir of infectious bacteria found in the oral cavity.

Since *S. mutans* are recalcitrant to antibiotic therapy in the biofilm phase, preventive approaches are considered safer and more practical. Currently, this approach relies mainly on prophylactic antibiotic therapy in high-risk patients. However, such treatments merely control the spreading of free bacteria (planktonic) and acute infections. Hence, the infections tend to be persistent, requiring multiple rounds of treatments to avoid permanent and lethal valve damage. Therefore, there exists a need for safer prophylactic approaches without the consequences of antibiotic therapy.

Competence Stimulating Peptide (CSP) is a natural peptide produced and secreted by *S. mutans* and acts as an autoinducer (Li, Y-H et al., *J. Bact.* 183:897–908 (2001). Competitive inhibitors of CSP have been investigated in relation to a method for the treatment of caries. Specifically, compounds that competitively inhibit the binding of CSP to *S. mutans* histidine kinase have been studied. (see U.S. Patent Application Publication No. 2002/0081302, which incorporated herein by reference). CSP is specific for *S. mutans* and functions exclusively as a regulator of many genes such as gtfB and gtfC and leads to repression of gtfB and gtfC gene expression. Glucosyltransferases (GTFs) are the products of these genes and are essential for efficient attachment of *S. mutans* to the surface of teeth. In the presence of their substrate (sucrose), GTFs catalyze the formation of long polymers of glucose called glucans, which are instrumental in the adherence of *S. mutans* to the surface of teeth. Once attachment is completed, the gtf genes are repressed and sucrose is utilized as energy source. The catabolism of sucrose results in the production of lactic acid that damages the tooth enamel and cause caries. The concentration of CSP is not naturally produced in significant quantities during the initial attachment to the tooth but is otherwise present after the adhesion is completed to ensure that gtfB and gtfC are repressed.

Since there is a strong association between the number of *S. mutans* in the oral cavity and the predisposition for tooth decay and endocarditis, a composition that can reduce the efficiency of *S. mutans* adherence should reduce or even eliminate the dental caries and endocarditis. Moreover, since early colonizing non-pathogenic oral bacteria rely on their own gtf genes for efficient adherence but are not affected by the presence of the *S. mutans* CSP, such bacteria will gain a competitive advantage over *S. mutans* if the ability of *S. mutans* to adhere to tooth surfaces is reduced

SUMMARY OF THE INVENTION

The present invention provides compositions, medicaments, and methods for treating and preventing conditions associated with the binding of *Streptococcus mutans* to teeth. More specifically, one aspect of this invention provides a composition for the prevention or prophylaxis of dental caries and endocarditis comprising *S. mutans* Competence Stimulating Peptide (*S. mutans* CSP) and sucrose. The compositions of this invention minimize the attachment of *S. mutans* to teeth, and consequently, minimize the negative consequences such as dental caries or endocarditis that could result from this attachment.

The compositions can be formulated with an orally acceptable carrier, and can be used in mouthwash solutions, abrasive dentifrice gels, chewing gums, nonabrasive dentifrice gels, soft drinks, and the like. The compositions can further comprise one or more anti-caries agents in addition to *S. mutans* CSP.

This invention further provides medicaments for the treatment or prophylaxis of conditions associated with the attachment of *S. mutans* to a subject's teeth. The medicament comprises *S. mutans* CSP in an amount effective to reduce the attachment of *S. mutans* to teeth. The medicament may further comprise at least one substance selected from the group consisting of sucrose, an orally acceptable carrier, an anti-caries agent in addition to CSP, and mixtures thereof.

Another aspect of the present invention provides a method for the treatment or prophylaxis of conditions associated with the attachment of *S. mutans* to a subject's teeth, comprising administering to a subject a composition or medicament of this invention containing *S. mutans* CSP in an amount effective to reduce the attachment of *S. mutans* to teeth. Conditions associated with the attachment of *S. mutans* to teeth include, but are not limited to, dental caries and infective endocarditis.

This invention provides safe and effective compositions and methods for reducing or eliminating the contribution of *S. mutans* to dental caries and endocarditis by reducing the reservoir of *S. mutans* in the oral cavity. In one embodiment, both pathologies are inhibited soon after the composition is applied. Further, the compositions of the present invention are non-toxic since CSP is already present in the oral cavity and only affects *S. mutans*. In addition, the compositions and medicaments can be used in very small quantities and therefore are inexpensive and easily affordable.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

BRIEF DESCRIPTION OF THE DRAWINGS

The accompanying drawings, which are incorporated in and form a part of the specification, illustrate non-limiting embodiments of the present invention, and together with the description serve to explain the principles of the invention.

In the Figures:

FIG. 1 is the sequence of the competence stimulating peptide (CSP) of *S. mutans*. The peptide sequence (SEQ ID NO: 1) is shown using the one-letter amino acid abbreviations from amino terminus to carboxyl terminus.

FIG. 10 shows the putative ComE binding sites in the upstream regions of gftB and gftC.

DETAILED DESCRIPTION OF THE INVENTION

Compositions

Figure 2:
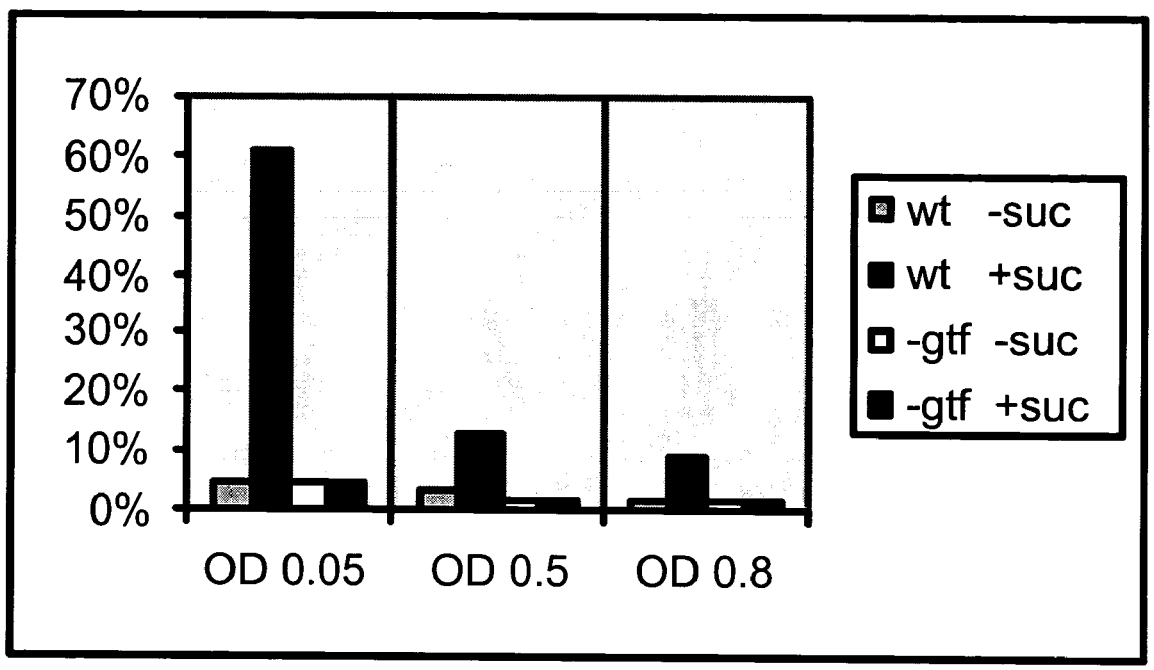
FIG. 2 is a bar graph of the data from an in vitro attachment assay presented as the percentage of attached bacteria verses optical density of the total (attached and unattached) bacteria.

One aspect of this invention provides compositions for the prevention or prophylaxis of oral diseases and endocarditis comprising *S. mutans* CSP (referred to hereinafter as CSP) and sucrose. The compositions of this invention minimize the attachment of *S. mutans* to teeth, and consequently, minimize the negative consequences such as dental caries and endocarditis that can result from this attachment. Since other early colonizing oral bacteria rely on their own gtf genes for efficient adherence and are not affected by the presence of CSP, such non-pathogenic bacteria will gain a competitive advantage over *S. mutans*. In one embodiment, the composition comprises between about 0.05 and 30% (w/w) of CSP.

It is to be understood all peptides and proteins having the same or similar function as the CSP peptide encoded by the sequence shown in FIG. 1 (SEQ ID NO: 1) are considered to be functional equivalents of this peptide and are also included within the scope of this invention. Accordingly, the terms "*S. mutans* CSP" and "CSP" as used herein encompass *S. mutans* and all functional equivalents thereof.

As stated, the CSP-containing compositions of this invention include sucrose. It was discovered that the negative effect of CSP on *S. mutans* is enhanced by the addition of sucrose. That is, since *S. mutans* is in direct competition with other early bacterial colonizers of the smooth surface of teeth and since many oral streptococci utilize similar glucosyltransferases to facilitate attachment, the combination of CSP and sucrose will specifically reduce the efficiency of *S. mutans* adherence while enhancing the ability of other non-pathogenic bacteria to more efficiently compete for the bare supergingival pellicle. Indeed, individuals that are edentate are devoid of *S. mutans*. Hence, CSP treatment should eventually lead to the surgical elimination of *S. mutans* from the oral cavity.

As used herein, the term "oral diseases" refers to diseases and disorders affecting the oral cavity or associated medical disorders that are caused by the attachment of *S. mutans* to a subject's teeth. Oral disorders include, but are not limited to, dental caries; periodontal diseases (e.g., gingivitis, adult periodontitis, early- onset periodontitis, etc.); mucosal infections (e.g., oral candidiasis, herpes simplex virus infections, oral human papillomavirus infections, recurrent aphtous ulcers, etc.); oral and pharyngeal cancers; and precancerous lesions.

The term "subject" refers to any animal, including mammals and humans.

The composition of this invention can further include one or more an anti-caries agents in addition to CSP. It is contemplated that various anti-caries reagents well known in the art can be included in the compositions and medicaments of the present invention and include, but are not limited to:

(1) substantially water insoluble noncationic antimicrobial agent, including but not limited to, Xylitol, triclosan, halogenated diphenyl ethers, benzoic esters; sesquiterpene alcohols (e.g., farnesol, nerolidol, bisabolol, and santalol); halogenated carbanilides, phenolic compounds including phenol and its homologs, mono-, poly-alkyl and aromatic halophenols, resorcinols (e.g., hexyl resorcinol), catechols (e.g., 2,2'-methylene bis (4-chloro-6-bromophenol), and bisphenolic compounds;

(2) non-steroidal anti-inflammatory drugs (NSAIDs), which can be characterized into five groups: (1) propionic acids (e.g., ibuprofen, indoprofen, ketoprofen, naproxen, benoxaprofen, flurbiprofen, fenoprofen, fenbufen, pirprofen, carpofen, oxaprozin, pranoprofen, miroprofen, tioxaprofen, suprofen, alminoprofen, tiaprofen, fluprofen, and bucloxic acid); (2) acetic acids (e.g., ketorolac, indomethacin, sulindac, tolmetin, zomepirac, diclofenac, fenclofenac, alclofenac, ibufenac, isoxepac, furofenac, tiopinac, zidometacin, acematacin, fentiazac, clidanac, oxpinac, and fenclozic acid); (3) fenamic acids (e.g., mefenamic acid, meclofenamic acid, flufenamic acid, niflumic acid, and tolfenamic acid): (4) biphenylcarboxylic acids (e.g., diflunisal and flufenisal); and (5) oxicams (e.g., piroxicam, sudoxicam and isoxicam);

(3) histidine-rich polypeptides ("HRPs," also referred to as histatins), such as histatin-based peptides disclosed in U.S. Pat. Nos. 4,725,576; 5,912,230; 5,885,965; 5,631,228; 5,646,119; and 5,486,503, each of which is incorporated herein by reference;

(4) fluorides reagents including sodium fluoride, stannous fluoride, amine fluorides, and monosodiumfluorophosphate;

(5) casein;

(6) plaque buffers such as urea, calcium lactate, calcium glycerophosphate, and strontium polyacrylates;

(7) non-immunogenic amino acid segments of proline-rich proteins that inhibit the adhesion of disease-causing microorganisms to tooth surfaces, as described in U.S. Pat. No. 5,013,542, incorporated herein by reference. The active ingredient can be derived from segmenting a natural or synthetic, proline-rich protein, to provide a non-immunogenic ingredient. The non-immunogenic amino acid segment can be obtained by various techniques, such as by cloning, or by synthesizing analogs of the natural molecules or their segments by chemical means. The non-immunogenic amino acid segment can also be obtained enzymatically or by cleaving the proline-rich protein derived from human saliva by the enzyme trypsin;

(8) antibodies of *S. mutans*, including intact molecules as well as functional fragments thereof, such as monoclonal IgG antibodies that specifically bind an antigen on the surface of *S. mutans*, including the following antibodies disclosed in U.S. Pat. No. 6,231,857, incorporated herein by reference: the hybridoma deposited with the American Type Culture Collection as ATCC No. HB12559 (designated SWLA1), the hybridoma deposited with the American Type Culture Collection as ATCC No. HB 12560, (designated SWLA2), and the hybridoma deposited with the American Type Culture Collection as ATCC No. HB 12258 (designated SWLA3). and (9) other pharmaceutically acceptable vehicles, diluents and additives such as antioxidants, buffers, bactericidal antibiotics and solutes which render the formulation isotonic in the intended recipient; and aqueous and non-aqueous sterile suspensions which may include suspending agents and thickening agents.

Oral Formulations

The compositions of this invention can be added to a variety of formulations suitable for delivery of the composition to the oral cavity, including, but not limited to, mouthwash solutions, abrasive dentifrice gels, nonabrasive dentifrice gels, denture washes or soaks, denture adhesives or cements, chewing gums, and soft drinks. In order to provide such formulations, a composition of this invention is combined with one or more orally acceptable carriers and/or excipients. Formulations including, but not limited to, mouth washes, abrasive or nonabrasive dentifrices, chewing gums, soft drinks, candies, and other orally acceptable compositions comprising CSP according to this invention can be prepared by any method known to persons skilled in the art. In general, methods of manufacturing anti-caries oral compositions comprise combining an orally acceptable carrier and an effective amount of CSP that can inhibit the expression of glucosyltransferases. A exemplary procedure for preparing an anti-caries oral composition in a gel formulation is provided in Example 9.

A variety of carriers and excipients can be used to formulate the compositions of this invention and are well known to those skilled in the art. Such orally acceptable vehicles for purposes of this invention include, but are not limited to, water, ethanol, humectants such as polypropylene glycol, glycerol and sorbitol, gelling agents such as cellulose derivatives (e.g., Methocel, carboxymethylcellulose (CMC 7MF) and Klucel HF), polyoxypropylene/polyoxyethylene block copolymers (e.g., Pluronic F-127, Pluronic F-108, Pluronic P-103, Pluronic P-104, Pluronic P-105 and Pluronic P-123), colloidal magnesium aluminosilicate complexes such as Veegum, and mucoprotein, thickening agents such as Carbopol 934, gel stabilizers such as silicon dioxides (e.g., Cab-O-Sil M5 and polyvinylpyrrolidone) sweeteners such as sodium saccharin and other approved flavors, preservatives such as citric acid, sodium benzoate, cetylpyridinium chloride, potassium sorbate, methyl and ethyl parabens, detergents such as sodium lauryl sulfate, sodium cocomonoglyceride sulfonate, sodium lauryl sarcosinate and polyoxyethylene isohexadecyl ether (Arlasolve 200), and approved colors.

Medicaments

Another aspect of this invention provides medicaments for the treatment or prophylaxis of a condition associated with the attachment of S. mutans to teeth, comprising CSP in an amount effective to reduce the attachment of S. mutans to teeth. An "effective amount" of CSP is the amount of compound that, when administered to a subject in need of treatment or prophylaxis, is sufficient to reduce the attachment of S. mutans to teeth and therefore, to treat or prevent conditions associated with the attachment of S. mutans to teeth. In one embodiment, the medicament comprises between about 0.05 and 30% (w/w) of CSP.

As used herein, the term "medicament" includes any type of medicament for administration to the oral cavity. In one embodiment the medicament can be a single dosage containing (1) CSP alone, (2) CSP in admixture with at least one additional agent effective against a condition associated with the attachment of S. mutans to teeth such as those described herein (3) CSP in admixture with sucrose, or (4) CSP in admixture with sucrose and at least one additional agent effective against a condition associated with the attachment of S. mutans to teeth.

Alternatively the medicament can be a kit with one or more dosage forms containing (1) CSP alone, (2) CSP and at least one additional agent effective against a condition associated with the attachment of S. mutans to teeth in admixture or in separate containers (3) CSP and sucrose in admixture or in separate containers, or (4) CSP, sucrose and at least one additional agent effective against a condition associated with the attachment of S. mutans to teeth, wherein the CSP, sucrose, and agent can be provided in separate vials or in admixture in any combination.

Method of Treatment

Another aspect of this invention provides a method for the prevention or prophylaxis of dental caries and endocarditis. In general, dental caries and infective endocarditis may be treated by contacting the oral cavity of a subject with an amount of S. mutans CSP effective to reduce or inhibit expression of the glucosyltransferase genes (gtfB and gtfC) either directly or indirectly, thereby reducing the attachment of S. mutans to the subject's teeth. In one embodiment, the CSP is formulated as an orally acceptable medicament as described herein comprising a carrier and an effective amount of CSP.

As used herein, the term "treating" is intended to mean at least the mitigation of a condition associated with the attachment of S. mutans to teeth in a subject, such as a human, that is affected at least in part by the condition, and includes, but is not limited to, modulating and/or inhibiting the condition; and/or alleviating the condition.

As used herein, the term "prophylaxis" is intended to mean at least preventing a condition associated with the attachment of S. mutans to teeth from occurring in a mammal, particularly when the mammal is found to be predisposed to having the condition but has not yet been diagnosed as having it.

With respect to dosage of CSP, whether alone or in combination with one or more additional anti-caries agents, one of ordinary skill in the art will recognize that a therapeutically effective amount will vary with the condition to be treated, its severity, the treatment regimen to be employed, the pharmacokinetics of the agent used, as well as the patient (animal or human) treated.

An exemplary dosing regime of an anti-caries composition or medicament of this invention is application of the composition or medicament to the oral cavity of the subject every time the subject eats a food containing sucrose. For example, people generally eat foods with sucrose from one to three times a day. According to this embodiment, a subject would apply a composition or medicament of this invention to the oral cavity from one to three times daily soon after consuming a sucrose-containing food or beverage as part of a routine oral hygiene program to inhibit or treat dental caries or as a program to prevent or treat endocarditis.

Since S. mutans is in direct competition with other early bacterial colonizers of the smooth surface of teeth and since many oral streptococci utilize similar glucosyltransferases to facilitate attachment, the presence of sucrose in any formulation of CSP should prove synergistic. Accordingly, the presence of sucrose in any CSP formulation or medicament of this invention will enhance the ability of glucosyltransferase dependent commensal bacteria to adhere. Thus, the combination of CSP and sucrose should both inhibit S. mutans attachment as well as facilitate the attachment of non-pathogenic bacteria, thus reducing the useable surface area and opportunity for S. mutans attachment. The plaque resulting from the attachment of non-pathogenic bacteria is benign and acts as a barrier for subsequent S. mutans attachment. Indeed, individuals that are edentate are devoid of S. mutans. Hence, CSP treatment should eventually lead to the surgical elimination of S. mutans from the oral cavity.

The foregoing aspects and features of the invention are further illustrated by the results of the examples discussed below. The examples are not to be construed as limiting of the invention in anyway. Thus, various modifications are possible within the scope of the invention.

EXAMPLES

Materials and Methods

1) Cultures

The results were obtained using two strains of S. mutans: GS5, its derivative GS5-gtfBCD (Hanada, N, Kuramitsu, H. K., *Infection and Immunity*, 57:2079–2085 (1989)), NG8 and its derivative NG8-comC (Li, Y-H et al., *J. of Bact.* 183:897–908 (2001)). In each assay the corresponding wild-type strain was used as a control for each mutant. However, where ascertainable, no difference between the two wild-type strains namely NG8 and GS5 was observed. The bacteria were cultured in liquid or solid Todd Hewitt medium at 37° C. with 5% $CO_2$ without agitation. The horse serum was added to 5% where indicated.

2) Transcriptional Fusions

The fusion constructs and the transcription assay were previously described (Goodman, S. D. and Gao, Q., *Plasmid* 43:85–98 (2000)). Briefly, the constructs comprised the upstream regions of the gtfB and gtfC genes fused to the promoterless coding sequence of the firefly luciferase gene and inserted into the plasmid vector pVA838, a shuttle plasmid capable of propagating in both *E. coli* and *S. mutans* marked with erythromycin resistance. The plasmids were introduced into *S. mutans* GS5 by electroporation and the resulting erythromycin resistant strains were grown in liquid cultures and collected at various optical densities. The reporter gene (luciferase) expression was detected by measuring luminescence upon the addition of luciferin (the substrate for luciferase), see Goodman, S. D. and Gao Q. Plasmid 42:154–157 (1999), incorporated herein by reference.

3) Attachment Assay

The bacteria were grown in liquid cultures to the desired optical density. 20 ml of the cultures were then transferred into Petri dishes and sucrose added to the final concentration of 2%. The incubation was resumed for one hour, after which the liquid fraction was withdrawn and the fresh medium was added into which the layer of attached cells was scraped. The percentage of the attached bacteria was determined as the ratio of the optical densities of the attached to the total (a sum of attached and unattached) bacteria.

4) Competition Assay

The gtfBCD mutant (erythromycin-resistant) and the wild-type *S. mutans* were mixed at an initial ratio of 1:1000. The resulting liquid culture was grown to the optical density of 0.1 (the peak of GTF activity and maximum attachment). At this optical density 20 mL of the bacteria were placed into the Petri dish containing sucrose and allowed to attach. After one hour 10 mL (one half) of the unattached bacteria were transferred into another Petri dish, diluted 1:1 with fresh medium and allowed to attach. The dilutions assured that the culture maintains a high level of gtf expression characteristic of the low cell density. The transfer was performed a total of three times. After the final attachment period the free bacteria were collected, diluted and plated on solid medium to get individual colonies. The colonies were then picked and tested for erythromycin resistance by streaking on solid medium containing erythromycin. The ratio of sensitive and resistance colonies was calculated to determine the resulting ratio of the mutant to wild-type bacteria.

5) Western Blotting

For the Western blotting, the bacteria were incubated to the desired optical density, subjected to the freeze-thaw cycle and mixed with the sample loading buffer. The samples were heated at 100° C. for 15 minutes and subjected to the PAGE. The number of cells per lane of the gel was kept constant at $10^8$ cells. The western blotting was performed in accordance with a standard procedure (Sambrook, J. and Russel D. W. Molecular Cloning, a laboratory manual, $3^{rd}$ ed. Cold Spring Harbor Laboratory Press, NY, 2001). Briefly, after PAGE the samples were transferred onto the nitrocellulose membrane and the latter subjected to the standard ELISA procedure. The anti-GTFB mouse monoclonal antibody was previously characterized (Fukushima, K., Okada, T., Ochiai, K., *Infection and Immunity* 61:323–328 (1993), incorporated herein by reference). The secondary antibody (HRP-linked goat anti-mouse) and the detection reagents were purchased from Cell Signaling Technology (Beverly, Mass.).

6) Addition of CSP to Bacterial Cultures

Synthetic CSP was dissolved in water to the concentration of 1 mg/mL as described in Li, Y-H et al., *J. of Bact.*, 183:897–908 (2001). The cultures were grown in Todd Hewitt Broth (THB) supplemented with 5% horse serum. CSP was added to the cultures at the time of diluting the overnight culture (time zero of the culture growth) to a designated concentration between 1 and 8 mcg/mL. The incubation then continued up to the optical density where the expression of GTF is maximal (OD 650=0.1). The cultures where then collected and used in Western blotting with anti-glucosyltransferase (gtf) antibody. A parallel Western blot was run with an anti-fructosyltransferase (ftf) antibody. The levels of FTF do not vary significantly during the growth of the culture. Cultures were also used for transcriptional fusion assays and for attachment assays.

7) Cloning and Expression of the *S. mutans* ComE Coding Sequence into *E. coli*

The DNA sequence of the comE gene is in the public domain and has a genbank accession number of AE015016.1. Oligonucleotides designed to be complimentary to the end points of the coding sequence were used to PCR amplify the intact coding sequence using *S. mutans* GS-5 chromosomal DNA as a template. The amplicon was then ligated into the Invitrogen (Carlsbad, Calif.) expression vector (pCR®T7TOPO®) according to the protocol of the manufacturer. In this genetic construction, comE is under the control of the plasmid's endogenous inducible promoter. *E. coli* strains either possessing the original plasmid or one with the new comE containing construction were grown to exponential growth and were treated with isopropylthiogalactoside which induces expression of the comE gene but only in this plasmid based system. After one hour of continued incubation, each culture was harvested, and lysed with lysozyme (0.4 mg/ml). Cell debris was pelleted by centrifugation and the remaining supernatant or cleared lysates were used for subsequent electromobility shift assays.

8) Electromobility Shift Assays with ComE Lysates

Electromobility shift assays (EMSA) were performed as described in Goodman et al., *J. of Bact.* 181:3246–3255 (1999). EMSA measures the extent of complexes formed at equilibrium between specific DNA sequences and proteins by the change in the rate of migration of the protein-DNA complex during gel electrophoresis as compared to the uncomplexed DNA. Complexed DNA migrates more slowly. For these experiments, a PCR DNA amplicon containing the promoter of gtfC and inclusive of the region from −89 to +103 (relative to the start of transcription designated as +1; the putative ComE site is located at −11 to +22) was used as the substrate for EMSA. Lysates of equivalent protein concentrations were used as the source of protein and added at 1:20 (v/v) to the reaction. Conditions for the formation of complexes and subsequent EMSA were performed as stated in Goodman et al., supra.

9) Techniques for detecting and quantitatively identifying *S. mutans* include bacterial culture with selective media using either broth or agar plate systems, and polymerase chain reaction techniques. (Ellen, R. P., *Oral Sci. Rev.* 8: 3–23 (1976); Igarashi et al., *Oral Microbiol. and Immunol.* 11: 294–298 (1996); U.S. Pat. No. 5,374,538; U.S. Pat. No. 4,692,407, each of which is incorporated herein by reference). Human dental caries may also be detected by changes in translucency, color, hardness or X-ray density of teeth. (U.S. Pat. No. 6,231,857, incorporated herein by reference).

EXAMPLE 1

An in vitro assay was performed as described in Materials and Methods to determine whether glucosyltransferases and their substrate (sucrose) are required for the *S. mutans* attachment to a smooth surface. The results are shown in FIG. 2, which shows that glucosyltransferases and sucrose are required for the *S. mutans* attachment. It was observed that when sucrose was added to the medium, the wild-type *S. mutans* readily attached to the surface of a Petri dish. The attachment was evidenced by the clearance of the substantial number of bacteria from the liquid medium and the presence of the increasing number of bacteria in the mucous layer synthesized on the surface of the Petri dish. After an hour-long incubation, up to 60% of bacterial cells were localized to the layer. On the contrary, the gtf-deficient mutant of *S. mutans* formed no such layer and less than 5% of cells were cleared from the liquid medium. In addition, the data demonstrate that the ability to attach is maximal during late-lag phase, decreases to 10% by the mid-log phase and falls below 5% as the culture reaches the stationary phase.

EXAMPLE 2

Figure 3:
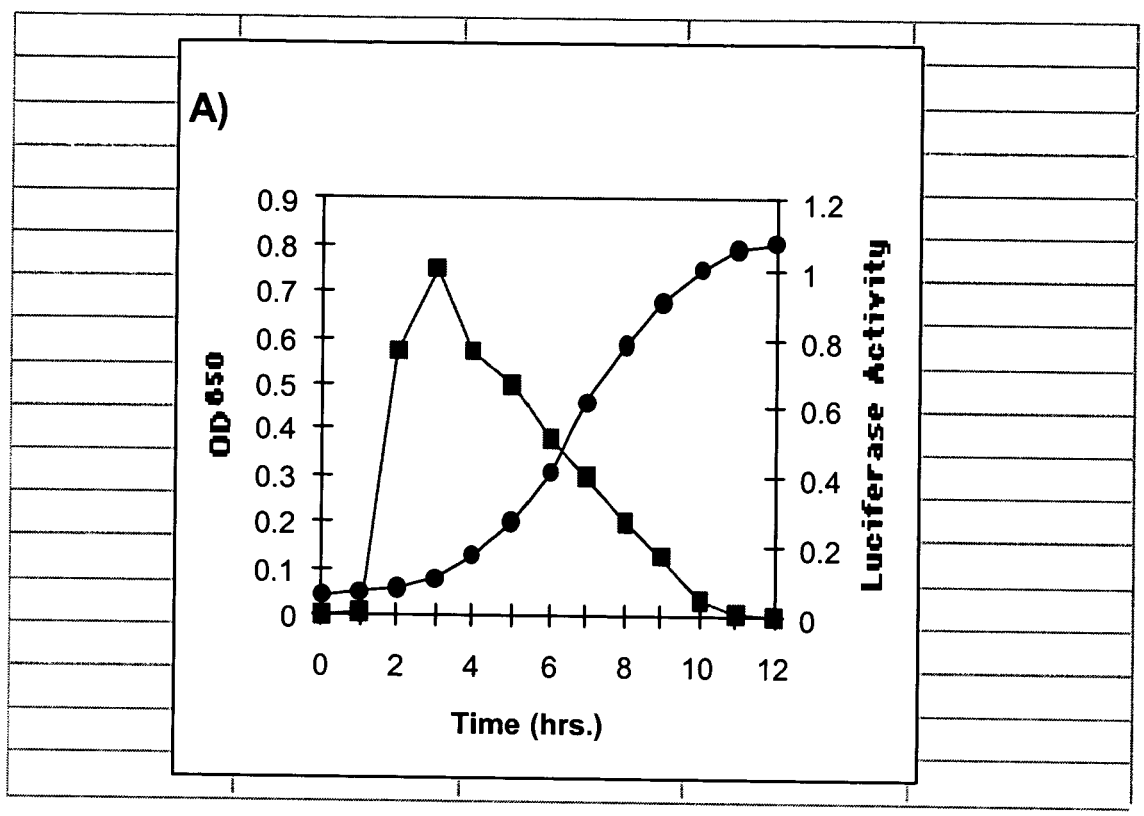
FIGS. 3A and 3B are graphs of the data from an in vivo transcriptional fusion assay of the growth phase-dependent expression of gftB (Panel A) and gftC (Panel B) genes in *S. mutans*, presented as optical density and luciferase activity verses time (hours).
Figure 3:
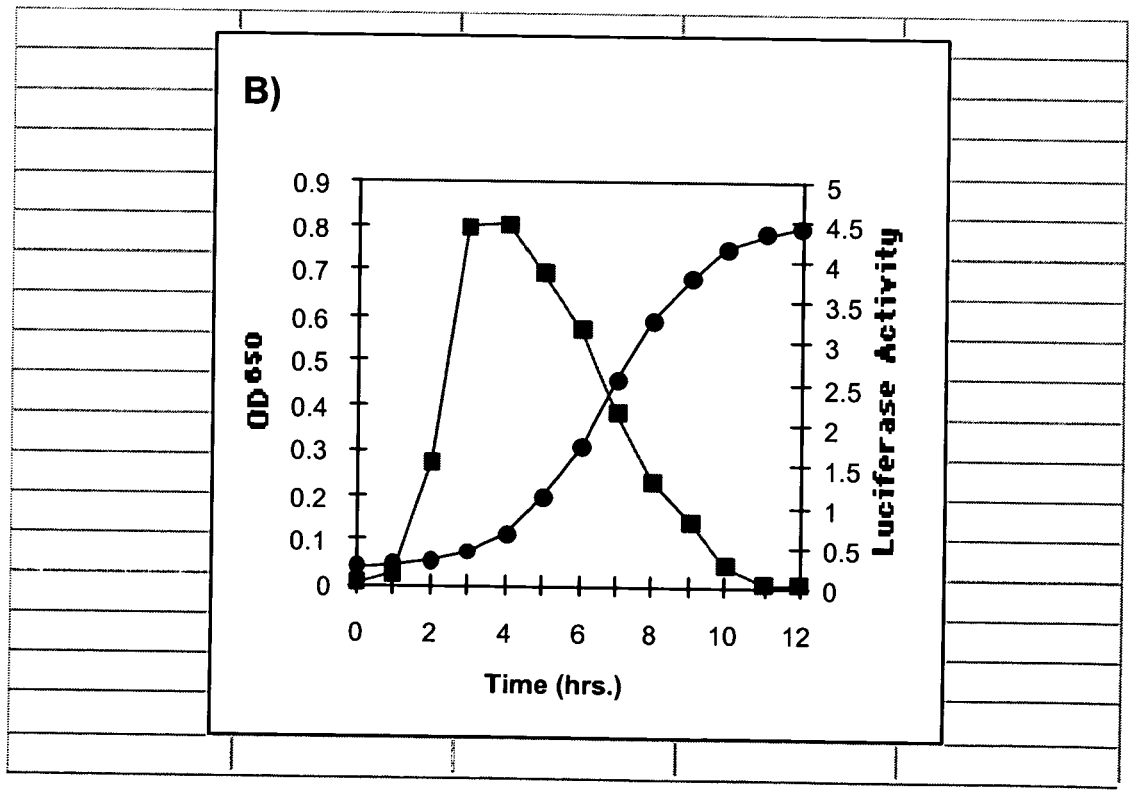

A transcriptional fusion assay was performed as described in Materials and Methods. The results are shown in FIGS. 3A and 3B. After the *S. mutans* culture was diluted, the expression was low in the stationary phase but rose rapidly as bacteria progress through the lag phase. The gtfB and gtfC expression peaked at the end of the lag phase prior to the exponential growth. The expression declined dramatically during the phase of exponential growth and returned to the low levels when the *S. mutans* culture reached the stationary phase. In addition, the data show that the two genes have separate functional promoters but are nevertheless regulated in the similar fashion. This example demonstrates the growth phase-dependent expression of gtfB and gtfC genes in *S. mutans*. This pattern reflects the role of these genes in the early events in the life of an *S. mutans* culture (e.g., at the time of the initial colonization of a tooth surface).

EXAMPLE 3

Figure 4:
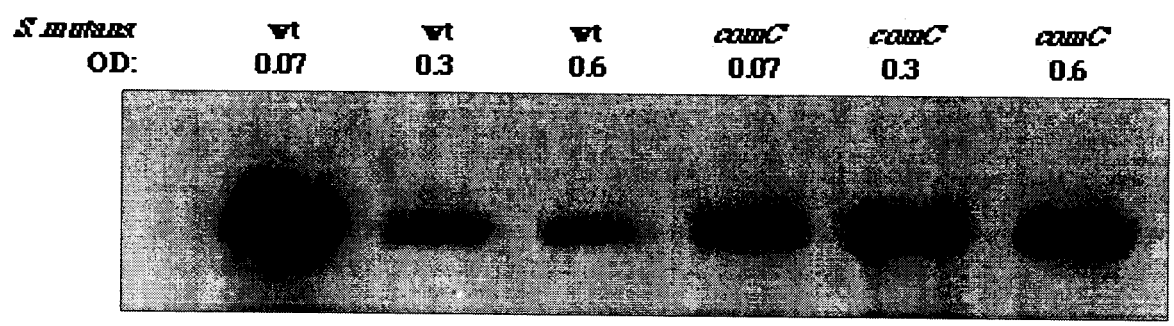
FIG. 4 is an image of a Western blot showing the overexpression of GTFB in the mutant of *S. mutans* lacking the CSP.

This example illustrates the role of CSP in regulating the gtfB gene. FIG. 4 is an image of a Western blot analysis using a monoclonal antibody against GTFB. As shown by FIG. 4, the normal pattern of GTFB expression is disrupted in the mutant *S, mutans* lacking the competence stimulating peptide (CSP). In the mutant *S. mutans*, the GTFB expression remained high throughout the growth of the culture. In contrast, in the wild-type, the amount of the protein was maximal in late lag phase and then dropped dramatically by the end of the exponential phase.

EXAMPLE 4

Figure 5:
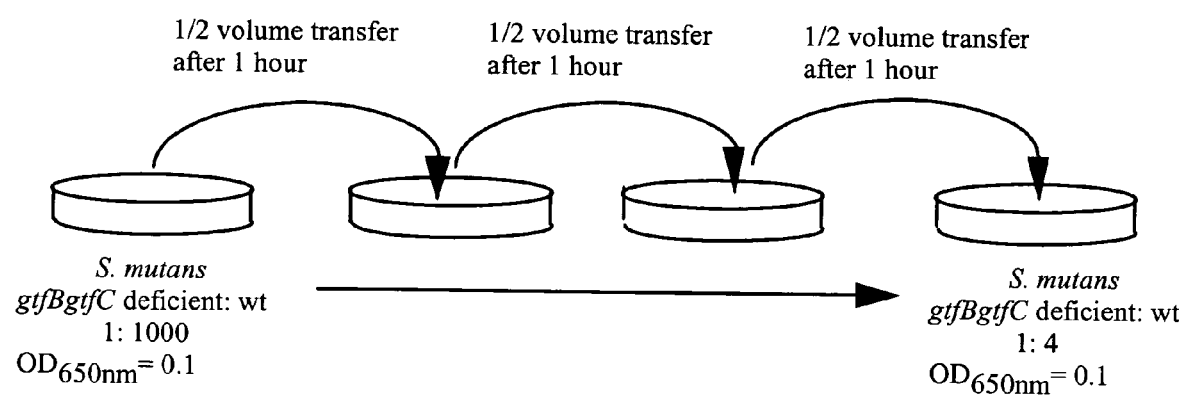
FIG. 5 is schematic representation of an in vitro attachment competition assay between the gftBCD (glucosyltransferase (gtf)-negative) mutant and wild-type *S. mutans*.

An in vitro competition assay was performed to demonstrate that the glucosyltransferase (gtf)-deficient mutant of *S. mutans* fails to attach to the surface in the presence of sucrose even when gtf-positive bacteria are present. The wild-type and mutant bacteria were mixed at an initial ratio of 1:1000. The unattached cells are periodically withdrawn and placed into a fresh dish. As shown in FIG. 5, after only three such passages the proportion of gtf-deficient bacteria in the supernatant increased 250-fold (from 1:1000 to 1:4). These results demonstrate that the GTF-expressing bacteria adhere to the surface while the GTF-deficient cells mostly remain in the liquid medium despite the fact that the glucans are available for attachment.

EXAMPLE 5

Figure 6:
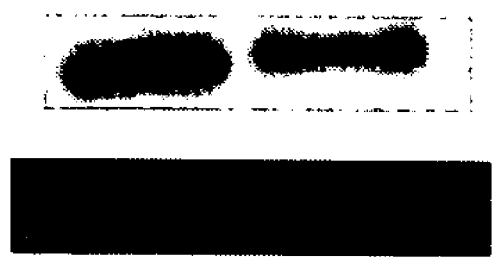
FIG. 6 is an image of a Western blot showing the negative effect of CSP on the GTFB expression in *S. mutans*.

A Western blot analysis was performed to determine the effect of CSP on the level of GTFB expression. As shown in FIG. 6, panel 1, CSP has a direct negative effect on the level of GTFB expression in the wild-type *S. mutans*. When CSP was added to the fresh cultures at the time of dilution, the peak expression of GTFB was lowered proportionally to the amount of peptide added. As a control, the same blot was analyzed with antibody specific to FTF, where it was observed that CSP has no effect on FTF expression (FIG. 6, panel 2).

EXAMPLE 6

Figure 7:
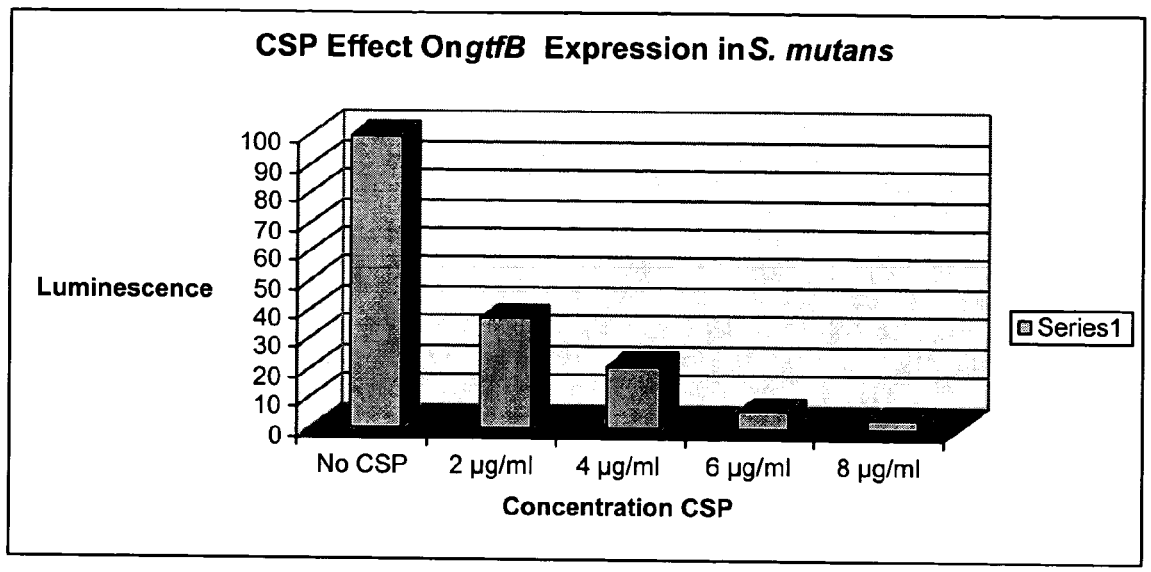
FIG. 7 is a bar graph of the data from a transcription fusion assay to determine the effect of CSP on gtfB gene expression in *S. mutans* presented as percent luminescence versus concentration of CSP.

The transcriptional fusion assay was performed to determine whether CSP inhibits the expression of the gtfB gene of *S. mutans*. *S. mutans* culture was first diluted from overnight cultures. The expression was low but rose rapidly as the bacteria progressed through the lag phase. When the expression peaked at the end of the lag phase prior to the exponential growth, the cells were challenged with increasing concentrations of CSP for an incubation period of 10 minutes and assessed for luminescence, the measure of reporter gene expression. As shown in FIG. 7, increasing concentrations of CSP increased the magnitude of repression. This example therefore demonstrates that CSP can inhibit the expression of at least the gtfB gene of *S. mutans*. The effect of CSP is consistent with repression at the level of transcription.

EXAMPLE 7

Figure 8:
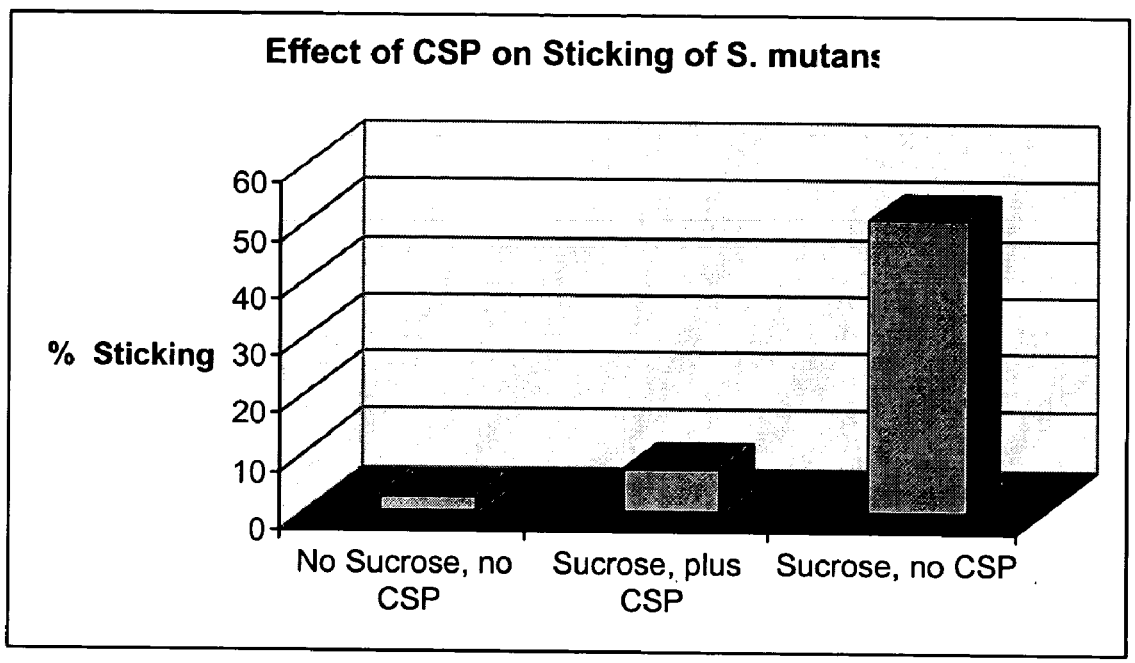
FIG. 8 is a bar graph of the percent of *S. mutans* that sticks to a surface in the presence of CSP and in the presence or absence of sucrose.

An in vitro assay was performed to determine whether CSP can inhibit the attachment of *S. mutans* to a smooth surface. When sucrose was added to the medium, the wild-type *S. mutans* readily attached to the surface of a Petri dish. The attachment was evidenced by the clearance of the substantial number of bacteria from the liquid medium and the presence of the increasing number of bacteria in the mucous layer synthesized on the surface of the Petri dish. *S. mutans* grown to an optical density consistent with the transition between lag and exponential growth for maximal expression of gftB and gtfC was utilized. As shown in FIG. 8, after an hour-long incubation up to 51% of bacterial cells were localized to the layer. On the contrary, when bacteria were challenged with CSP at 8 μg/mL for 10 minutes prior to incubation on Petri dishes, *S. mutans* formed much less of a layer (less than 8%). This example therefore demonstrates that CSP can inhibit the attachment of *S. mutans* to a smooth surface.

EXAMPLE 8

Figure 9:
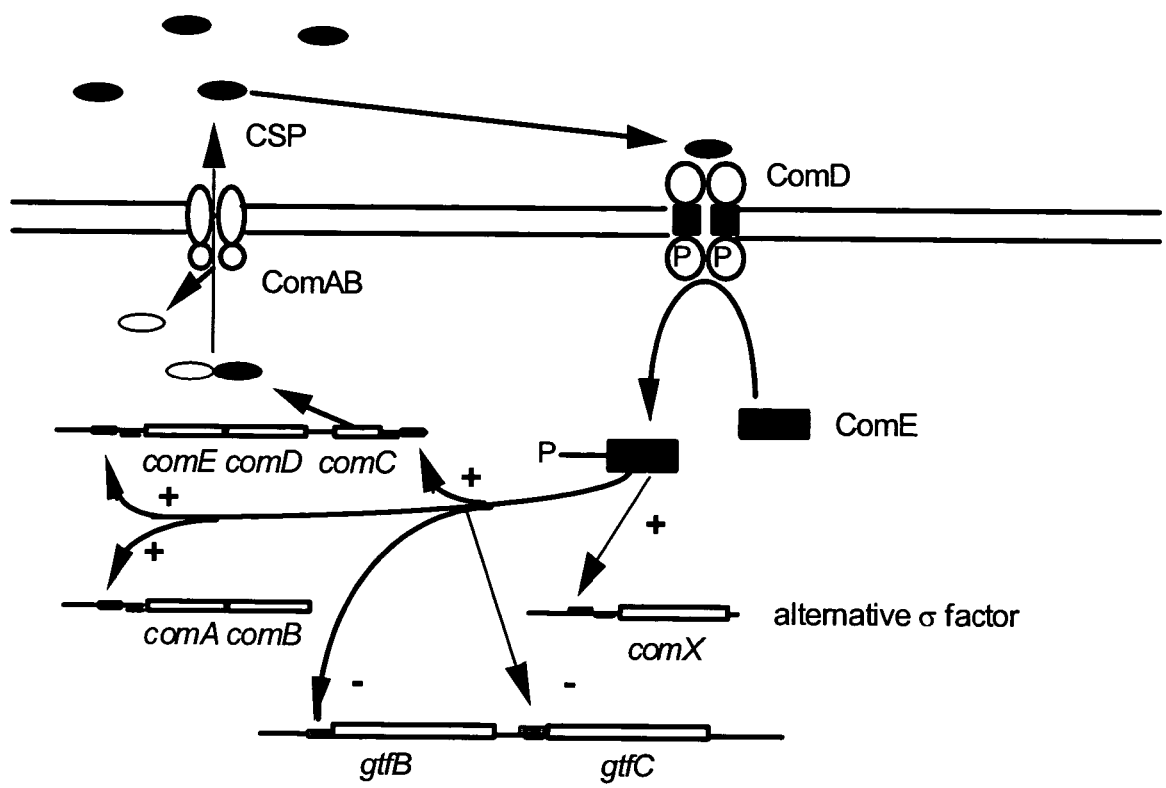
FIG. 9 is the postulated regulation of gtf genes by the competence pathway.

The putative regulatory pathway controlling the glucosyltransferase (gtf) gene expression is illustrated in FIG. 9. The competence stimulating peptide (CSP) is cleaved off of a larger peptide which is the product of the comC gene. CSP is extruded into the extracellular milieu by the specific transporter ComAB (the two components are the products of the genes comA and comB). The extracellular concentration of CSP increases with the increase in cell density. When the concentration reaches a threshold, CSP activates its specific receptor ComD. ComD in turn activates a response regulator ComE by phosphorylation. ComE modulates gene expression by binding to its target sites in the regulatory regions on the DNA. ComE regulator has been studied in a related species of the genus Streptococci: S. pneumoniae. In that system it has been shown that ComE interacts with its specific binding sites in the upstream regions of several genes and operons: comC, comX (an alternative sigma factor, a transcription factor), comAB, and comED. (Lee, M. S. and Morrison, D. A., *J. of Bact.*, 181:5004–5016 (1999)).

The inventors have shown that the putative ComE binding sites exist in the upstream regions of both gtfB and gtfC FIG. 10. In both gtfB and gtfC, promoter regions the ComE box can be found at −11 base of the promoter region. In FIG. 10, capital letters represent actual DNA sequence for gtfB and gtfC while they represent conserved sequence in a ComE consensus derived from the genus streptococcus. Lower case letters are less conserved DNA sequence. The letter W represents either an adenine or thymidine base pair. The asterisk (*) represents a potential one base pair gap in the DNA sequence alignment. This result points at the likelihood that CSP regulates gtf expression via the ComE pathway.

Figure 11:
FIG. 11 is an image of an electromobility shift assay gel. Lane 1 is gtfC promoter DNA; Lane 2 is gtfC promoter DNA with *E. coli* cleared lysate added; and Lane 3 is gtfC promoter DNA with *E. coli* cleared lysate containing *S. mutans* ComE.
Figure 11:

As evidence of this model, *E. coli* cleared lysates either possessing ComE or lacking ComE were used in an electromobility shift assay (EMSA) to assess the capacity of these lysates to bind to the gtfC promoter region that contains the streptococcal ComE box FIG. 11. Lysates that did not possess expressed ComE failed to form complexes with the gtfC promoter despite possessing a plethora of other *E. coli* proteins. It is believed that it is the ComE protein which is the only component that distinguishes these two lysates and creates the complex.

EXAMPLE 9

This example provides an exemplary procedure for preparing a formulation comprising CSP according to this invention. Water, sodium saccharin, sodium benzoate and dyes are combined in a first container and the container is place in an ice bath. When the temperature reaches 6° C., a gelling agent is added. The contents are mixed slowly until the gelling agent is dissolved, and then the solution is heated to 70° C. Into a second container is added glycerin, and then Cab-O-Sil M5 is sprinkled in with mixing. CSP is then added and mixing is continued to a smooth paste. The paste is then heated in a water bath with mixing to a temperature of 70° C.

The contents of the first container are added to the second container and blended together until the batch is homogenous while maintaining a 70° C. temperature. A flavoring agent is then added, mixing is stopped, and the formulation allowed to settle for approximately one hour. If necessary, the formulation can be refrigerated overnight refrigeration to remove air bubbles.

CSP can be produced in either of two ways. It is naturally secreted during exponential growth of *S. mutans*. Fermentation of the bacteria will result in the media being saturated with CSP. Spent or conditioned media can then be further purified or used directly. Alternatively, the peptide can be synthesized according to automated peptide synthesis procedures known in the art, such as the well known Merrifield method, as described in Merrifield, R. B. *J. Am. Chem. Soc.* 85:2149 (1963); and Merrifield, R. B. *Science*, 232:341 (1986), each of which is specifically incorporated herein by reference.

EXAMPLE 10

This example provides an example of a mouthwash formulation according to this invention containing CSP.

| Ingredient | Amount (% w/w) |
| --- | --- |
| CSP | 0.5–2.0 |
| Glycerol (humectant) | 6.0 |
| Pluronic F-108 | 1.0 |
| Sodium saccharin (sweetener) | 0.3 |
| Deionized Water | q.s. |
| Flavors | 1.0 |
| | 100.0 |

EXAMPLE 11

This example provides another example of a mouthwash formulation according to this invention containing CSP.

| Ingredient | Amount (% w/w) |
| --- | --- |
| CSP | 0.5–3.0 |
| Ethanol, USP 1 | 5.0 |
| Pluronic F-108 (foaming agent) | 2.0 |
| Glycerol (humectant) | 10.0 |
| Sorbitol (humectant) | 10.0 |
| Sodium saccharin (sweetener) | 0.2 |
| Deionized Water | q.s. |
| Flavors | 0.2 |
| | 100.0 |

EXAMPLE 12

This example provides another example of an abrasive dentifrice gel formulation according to this invention containing CSP.

| Ingredient | Amount (% w/w) |
| --- | --- |
| CSP | 2.0–10.0 |
| Fumed Silica (abrasive) | 55.0 |
| Sodium Lauryl Sulfate (detergent) | 1.5 |
| Glycerol (humectant) | 10.0 |
| Carboxymethylcellulose (gelling agent) | 2.0 |
| Sodium saccharin (sweetener) | 0.2 |
| Sorbitol (humectant) | 10.0 |
| Flavors | 1.0 |
| Deionized Water | q.s. |
| Preservative | 0.05 |
| | 100.0 |

EXAMPLE 13

This example provides an example of a chewing gum formulation according to this invention containing CSP.

| Ingredient | Amount (% w/w) |
| --- | --- |
| CSP | 1.0–11.0 |
| Gum Base | 21.3 |
| Sucrose | 48.5–58.5 |
| Corn Syrup (Baume 45) | 18.2 |
| Flavors | 1.0 |
| | 100.0 |

EXAMPLE 14

This example provides an example of a nonabrasive gel dentifrice formulation according to this invention containing CSP.

| Ingredient | Amount (% w/w) |
| --- | --- |
| CSP | 0.05–30.0 |
| Sorbistat (preservative) | 0.15 |
| Deionized Water | q.s. |
| Silicon Dioxide (gel stabilizer) | 1.0 |
| Pluronic F-127 (gelling agent) | 20.0 |
| Sodium Saccharin | 0.2 |
| Flavors | 1.5 |
| | 100.0 |

EXAMPLE 15

This example provides another example of a nonabrasive gel dentifrice formulation according to this invention containing CSP.

| Ingredient | Amount (% w/w) |
| --- | --- |
| Distilled Water | q.s. |
| Sodium Saccharin (sweetener) | 0.20 |
| Sodium Benzoate (preservative) | 0.30 |
| FD&C Blue #1 (0.1% aq. soln.) | 0.27 |
| D&C Yellow #10 (0.5% aq. soln.) | 0.50 |
| Gelling agent | 18.00 |
| Glycerol (Humectant) | 20.00 |
| Cab-O-Sil M5 (Silicon Dioxide) | 1.00 |
| CSP | 5.00 (dry basis) |
| Flavor | 0.80 |
| | 100.0 |

EXAMPLE 16

This example provides an example of a soft drink formulation according to this invention containing CSP.

Ingredient

Distilled Water
Carbon Dioxide
Sucrose
Flavors
Colors
Caffeine
Acidulants
Preservatives
Potassium
Sodium
CSP

EXAMPLE 17

This example provides an example of a candy formulation according to this invention containing CSP.

Ingredient

Distilled Water
Leavening agents
Stabilizers
Thickeners
Sucrose
Flavors
Colors
Acidulants
Preservatives
Antioxidants
CSP While the above description contains many specificities, these should not be construed as limitations on the scope of the invention, but rather an exemplification of the preferred embodiment thereof. Many other variations are possible, such as amplifying several target samples in the same reaction mixture, isothermal amplification, utilizing newly discovered polymerases and ligases, etc. Thus the scope of the invention should be determined by the appended claims and their legal equivalents, rather than by the example given.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A composition comprising an isolated Competence Stimulating Peptide (CSP) and sucrose, wherein the CSP comprises SEQ ID NO:1, wherein the composition is capable of preventing attachment of *S. mutans* to teeth.

2. The composition according to claim 1, further comprising at least one substance selected from the group consisting of an orally acceptable carrier, an anti-caries agent, and mixtures thereof.

3. The composition according to claim 1, further comprising an orally acceptable carrier and an anti-caries agent.

4. The composition according to claim 1, wherein the CSP in the composition is present in an amount from about 0.05% to about 30% w/w.

5. The composition according to claim 1, wherein the composition is in a form selected from the group consisting of a mouthwash solution, an abrasive dentifrice gel, a chewing gum, a nonabrasive dentifrice gel, a nonabrasive gel composition, and a soft drink.

6. The composition according to claim 2, wherein the anti-caries agent is selected from the group consisting of water insoluble noncationic antimicrobial agents, non-steroidal anti-inflammatory drugs, fluoride reagents, histidine-rich polypeptides, casein, urea, calcium lactate, calcium glycerophosphate, non-immunogenic amino acid segments of proline-rich proteins, monoclonal antibodies against *S. mutans*.

7. A medicament for the treatment or prophylaxis of a condition associated with the attachment of *S. mutans* to teeth, comprising an isolated CSP in an amount effective to reduce the attachment of *S. mutans* to teeth, wherein the CSP comprises SEQ ID NO:1.

8. The medicament of claim 7, wherein the medicament further comprises at least one substance selected from a group consisting of sucrose, an orally acceptable carrier, an anti-caries agent, and mixtures thereof.

9. The medicament of claim 7, wherein the medicament further comprises sucrose.

10. The medicament of claim 7, wherein the medicament further comprises sucrose, an orally acceptable carrier, and an anti-caries agent.

11. The medicament of claim 7, wherein the CSP is present in an amount between about 0.05% to about 30% w/w.

12. The medicament of claim 7, wherein the condition is selected from the group consisting of dental caries or endocarditis.

13. The medicament of claim 8, wherein the anti-caries agent is selected from the group consisting of water insoluble noncationic antimicrobial agents, non-steroidal anti-inflammatory drugs, fluoride reagents, histidine-rich polypeptides, casein, urea, calcium lactate, calcium glycerophosphate, non-immunogenic amino acid segments of proline-rich proteins, monoclonal antibodies against *S. mutans*.

14. A composition comprising an isolated Competence Stimulating Peptide (CSP) and sucrose, wherein the CSP consists of SEQ ID NO: 1.

15. A medicament for the treatment or prophylaxis of a condition associated with the attachment of *S. mutans* to teeth, comprising an isolated CSP in an amount effective to reduce the attachment of *S. mutans* to teeth, wherein the CSP consists of SEQ ID NO:1.

16. The composition according to claim 1, wherein the composition stimulates attachment of non-pathogenic bacteria to the teeth.

* * * * *

UNITED STATES PATENT AND TRADEMARK OFFICE
CERTIFICATE OF CORRECTION

| | |
|---|---|
| PATENT NO. | : 7,087,228 B2 |
| APPLICATION NO. | : 10/614072 |
| DATED | : August 8, 2006 |
| INVENTOR(S) | : Steven D. Goodman et al. |

Page 1 of 1

It is certified that error appears in the above-identified patent and that said Letters Patent is hereby corrected as shown below:

Col. 1, line 12, insert the following: -- STATEMENT REGARDING FEDERALLY SPONSORED RESEARCH OR DEVELOPMENT
   This invention was made with government support under Contract No. DE011875 awarded by the National Institutes of Health. The government has certain rights in the invention. --

Signed and Sealed this

Eleventh Day of August, 2009

David J. Kappos
*Director of the United States Patent and Trademark Office*

SEQUENCE LISTING

```
<160> NUMBER OF SEQ ID NOS: 1

<210> SEQ ID NO 1
<211> LENGTH: 21
<212> TYPE: PRT
<213> ORGANISM: Streptococcus mutans

<400> SEQUENCE: 1

Ser Gly Ser Leu Ser Thr Phe Phe Arg Leu Phe Asn Arg Ser Phe Thr
1               5                   10                  15

Gln Ala Leu Gly Lys
            20
```